US012514787B2

(12) United States Patent
Okihara

(10) Patent No.: US 12,514,787 B2
(45) Date of Patent: Jan. 6, 2026

(54) SYRINGE SET AND SYRINGE HAVING A REMOVABLE BLOCKING MEMBER

(71) Applicant: TERUMO KABUSHIKI KAISHA, Tokyo (JP)

(72) Inventor: Hitoshi Okihara, Susono (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 778 days.

(21) Appl. No.: 17/869,331

(22) Filed: Jul. 20, 2022

(65) Prior Publication Data

US 2022/0354747 A1 Nov. 10, 2022

Related U.S. Application Data

(63) Continuation of application No. PCT/JP2021/008877, filed on Mar. 8, 2021.

(30) Foreign Application Priority Data

Mar. 9, 2020 (JP) ................................ 2020-039723

(51) Int. Cl.
*A61J 1/20* (2006.01)
*A61M 5/00* (2006.01)
(Continued)

(52) U.S. Cl.
CPC ........... *A61J 1/2096* (2013.01); *A61J 1/2055* (2015.05); *A61M 5/002* (2013.01);
(Continued)

(58) Field of Classification Search
CPC ............ A61M 5/002; A61M 2005/3104; A61J 1/1418; A61J 1/2089; A61J 1/2096
See application file for complete search history.

(56) References Cited

U.S. PATENT DOCUMENTS 6,003,566 A 12/1999 Thibault et al.
2003/0018303 A1* 1/2003 Sharp .................. A61M 5/3202 604/192
(Continued)

FOREIGN PATENT DOCUMENTS

CN 1225574 A 8/1999
JP 2004-089446 A 3/2004
(Continued)

OTHER PUBLICATIONS

English Translations of the International Search Report (Form PCT/ISA/210) and the Written Opinion of the International Searching Authority (Form PCT/ISA/237) issued May 11, 2021, by the Japan Patent Office in corresponding International Application No. PCT/JP2021/008877. (6 pages).
(Continued)

*Primary Examiner* — Kami A Bosworth
(74) *Attorney, Agent, or Firm* — BUCHANAN INGERSOLL & ROONEY PC

(57) ABSTRACT

A syringe set includes a first syringe having a first connection port and a drug container having a second connection port. The first connection port includes an injection needle attachment structure to which an injection needle is attachable, and a blocking member that is disposed in the injection needle attachment structure and blocks attachment of the injection needle. When the second connection port is connected to the first connection port, the blocking member is connected to the second connection port side, and when the second connection port is detached, the blocking member is detached from the first connection port so as to allow the injection needle to be attached to the first connection port.

18 Claims, 15 Drawing Sheets

(51) Int. Cl.
*A61M 5/32* (2006.01)
*A61M 5/34* (2006.01)

(52) U.S. Cl.
CPC .......... *A61M 5/3202* (2013.01); *A61M 5/344* (2013.01); *A61M 2207/00* (2013.01)

(56) References Cited

U.S. PATENT DOCUMENTS

| | | | | |
|---|---|---|---|---|
| 2009/0082725 | A1* | 3/2009 | Witowski ............ | A61M 5/5086 604/111 |
| 2012/0123382 | A1 | 5/2012 | Kubo | |
| 2015/0060462 | A1* | 3/2015 | Colbert ................. | A61J 1/2096 424/94.67 |
| 2016/0095988 | A1 | 4/2016 | Fraas | |
| 2018/0117264 | A1 | 5/2018 | Hirobe | |

FOREIGN PATENT DOCUMENTS

| | | | |
|---|---|---|---|
| JP | 2011-072440 | A | 4/2011 |
| JP | 2011194045 | A | 10/2011 |
| JP | 2013132349 | A | 7/2013 |
| JP | 2014079331 | A | 5/2014 |
| JP | 2014-200504 | A | 10/2014 |
| JP | 2014200505 | A | 10/2014 |
| WO | 2016181826 | A1 | 11/2016 |

OTHER PUBLICATIONS

International Search Report (PCT/ISA/210) with translation and Written Opinion (PCT/ISA/237) mailed on May 11, 2021, by the Japan Patent Office as the International Searching Authority for International Application No. PCT/JP2021/008877.

The extended European Search Report issued Aug. 7, 2023, by the European Patent Office in corresponding European Patent Application No. 21768244.2-1122. (127 pages).

Office Action (The First Office Action) issued on Mar. 12, 2025, in corresponding Chinese Patent Application No. 202180007415.X and machine English translation of the Office Action. (18 pages).

Search Report issued on Mar. 10, 2025, in corresponding Chinese Patent Application No. 202180007415.X. (3 pages).

* cited by examiner

SYRINGE SET AND SYRINGE HAVING A REMOVABLE BLOCKING MEMBER

CROSS-REFERENCES TO RELATED APPLICATIONS

This application is a continuation of International Application No. PCT/JP2021/008877 filed on Mar. 8, 2021, which claims priority to Japanese Patent Application No. 2020-039723 filed on Mar. 9, 2020, the entire content of both of which is incorporated herein by reference.

TECHNOLOGICAL FIELD

The present invention generally relates to a method as well as a syringe set, a syringe, and a set to be used for an injection to be prepared by mixing drugs before use.

BACKGROUND DISCUSSION

An injection is known in which two drugs that are separately stored are mixed together and then used. Such an injection is provided, for example, in such a manner that one drug is enclosed in a vial container or a syringe as a powder and the other drug is enclosed in a syringe for injection as a solution such as water for injection or physiological saline. An example is disclosed in Japanese Patent Application Publication No. 2013-132349.

The injection is prepared by connecting one syringe (or vial) to the other syringe for injection and mixing the two drugs while operating a plunger of the syringe for injection. Then, the prepared injection is transferred to the syringe for injection, the syringe (or vial) is removed, and an injection needle is attached to the syringe for injection to perform administration.

SUMMARY

The work associated with preparing an injection is performed not only by a medical institution but also by a patient at home in some cases. When the patient himself/herself administers an injection, there is a case where the patient forgets to mix the drugs. In such a case, there is a possibility that the patient erroneously recognizes a drug (for example, a solution such as an injection solution or physiological saline) enclosed in a syringe for injection as a prepared drug, attaches an injection needle to a syringe and erroneously administers the drug without performing the mixing operation.

Disclosed here are a syringe set, a syringe, and a set capable of preventing erroneous administration of an injection that is to be prepared by mixing drugs before use, due to forgetting of mixing the drugs.

According to one aspect, there is provided a syringe set including: a first syringe including a barrel having an inside in which is stored a liquid first drug, with the first syringe including a first connection port at a distal end of the barrel and the first connection port communicating with the inside of the barrel; and a drug container having an inside in which is stored a second drug, with the drug container including a second connection port that is connectable to and detachable from the first connection port of the first syringe. The first connection port of the first syringe includes an injection needle attachment structure configured to be attached to an injection needle, and a blocking member disposed in the injection needle attachment structure and configured to block attachment of the injection needle to the injection needle attachment structure when the blocking member is disposed in the injection needle attachment structure. The blocking member is detachable from the first connection port to remove the blocking member from the injection needle attachment structure and permit attachment of the injection needle to the injection needle attachment structure. The blocking member is connectable to a part of the second connection port when the second connection port is connected to the first connection port, and the blocking member is detached from the first connection port when the second connection port to which the blocking member is connected is detached from the first connection port, thereby allowing the injection needle to be attached to the injection needle attachment structure.

According to another aspect, there is provided a syringe that is connectable to a drug container in which is stored a drug immediately before use and that is used for administration after a liquid drug inside the syringe is mixed with the drug stored in the drug container. The syringe comprises: a barrel in which is stored the liquid drug; a first connection port at a distal end of the barrel and configured to be connected to the drug container so that the syringe is connected to drug container and the liquid drug stored in the barrel of the syringe mixes with the drug stored in the drug container; wherein the first connection port includes an injection needle attachment structure configured to be attached to an injection needle, and a blocking member disposed in the injection needle attachment structure and configured to block attachment of the injection needle to the injection needle attachment structure when the blocking member is disposed in the injection needle attachment structure, with the blocking member being detachable from the first connection port to remove the blocking member from the injection needle attachment structure and permit attachment of the injection needle to the injection needle attachment structure. The blocking member is connectable to the drug container when the drug container is connected to the syringe, and the blocking member is detached from the first connection port when the drug container to which the blocking member is connected is detached from the first connection port, thereby allowing the injection needle to be attached to the injection needle attachment structure.

According to still another aspect, there is provided a method comprising connecting a syringe having an inside in which is stored a liquid first drug and a drug container having an inside in which is stored a second drug, wherein the syringe comprises an injection needle attachment structure configured to be connected to an injection needle, and the syringe also comprises a blocking member disposed in the injection needle attachment structure to block attachment of the injection needle to the injection needle attachment structure by virtue of the blocking member being contacted by a portion of the injection needle. The connecting of the syringe to the drug container including connecting a portion of the drug container to the blocking member, and communicating the inside of the drug container with the inside of the syringe to mix the first drug and the second drug. The method additionally includes: disconnecting the drug container and the syringe from one another while the mixed first and second drugs are in the inside of the syringe so that the drug container and the syringe are separated from one another, with the disconnecting of the drug container and the syringe from one another causing the blocking member to be removed from the injection needle attachment structure; and connecting the injection needle to the syringe by causing the portion of the injection needle to engage the injection needle attachment structure, whereby a needle tube of the injection needle communicates with the inside of the syringe so that the mixed first and second drugs can flow into the needle tube.

According to the syringe set, the syringe, and the method from the above viewpoints, the injection needle is not attached if mixing is forgotten, so that it is possible to prevent erroneous administration due to forgetting of mixing.

DETAILED DESCRIPTION

Set forth below with reference to the accompanying drawings is a detailed description of embodiments of a syringe set, a syringe, and a set representing examples of the new syringe set, syringe, and set disclosed here.

First Embodiment

Figure 1:
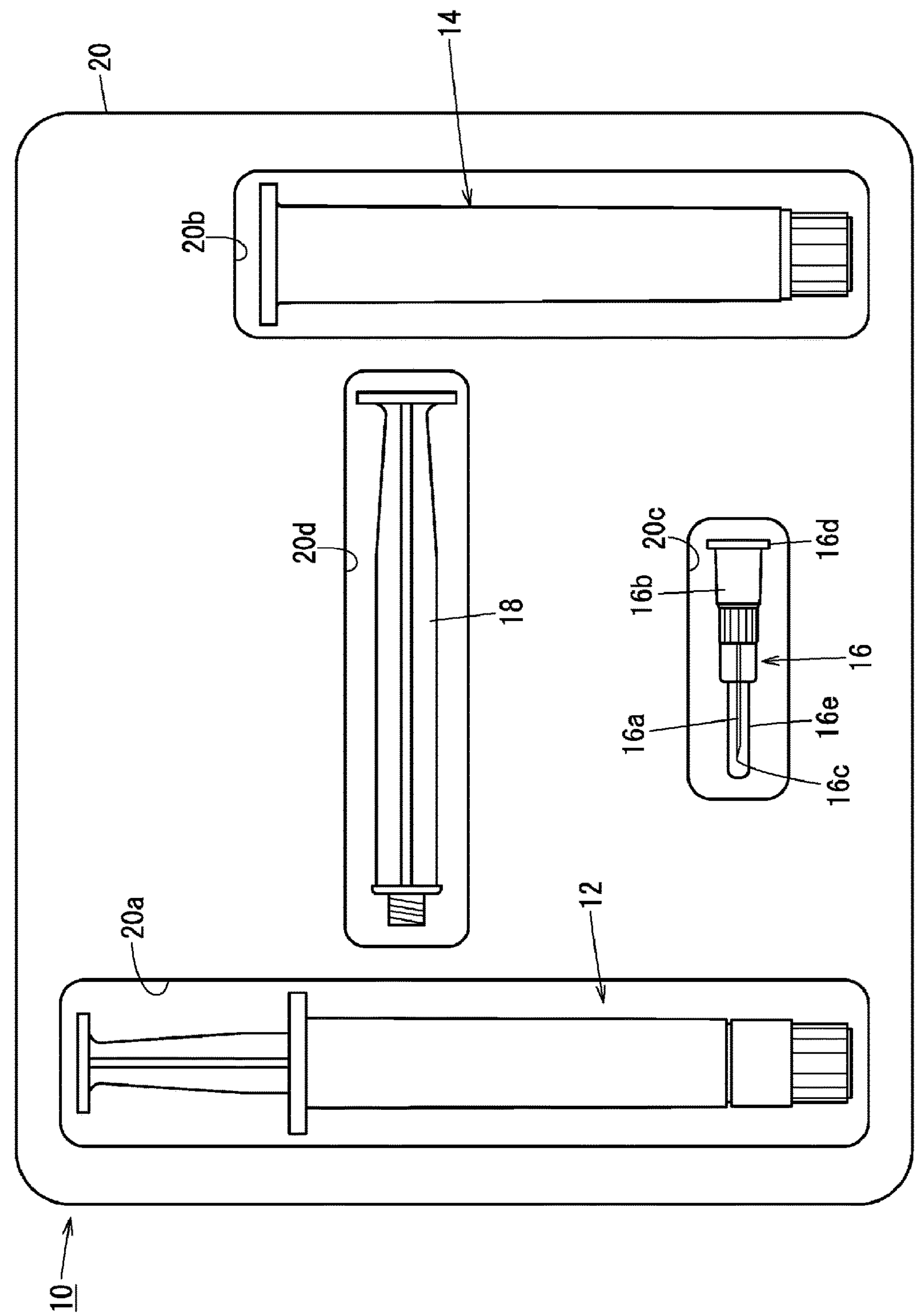
FIG. 1 is a plan view of a syringe set according to a first embodiment.

A syringe set 10 according to the present embodiment is used for an injection to be prepared by mixing two types of drugs that are separately stored and includes a first syringe 12 (syringe), a second syringe 14, and an injection needle 16 as illustrated in FIG. 1. The first syringe 12 and the second syringe 14 store different types of drugs, respectively.

The first syringe 12, the second syringe 14, and the injection needle 16 are provided to a user in a state where they are accommodated in a tray 20 having a plurality of accommodation recesses 20*a* to 20*d*. Although not particularly limited, a second plunger 18 of the second syringe 14 is separated from the second syringe 14 and accommodated in the accommodation recess 20*d*. The second plunger 18 may be assembled to the second syringe 14 in advance.

Figure 2A:
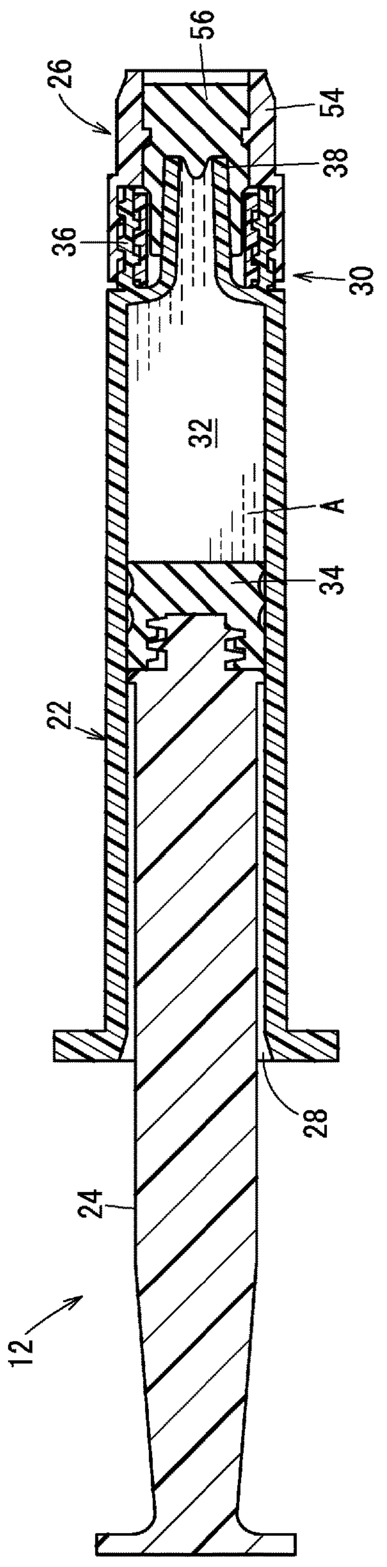
FIG. 2A is a cross-sectional view of a first syringe of FIG. 1.

As illustrated in FIG. 2A, the first syringe 12 includes a first barrel 22, a first plunger 24, and a first cap 26. Among them, the first barrel 22 is formed in a cylindrical shape, a first opening portion 28 is formed on a proximal end side, and a first connection port 30 is formed on a distal end side. Inside of the first barrel 22 is a first storage chamber 32 that stores a drug. The first barrel 22 is fabricated from a transparent resin so as to allow a state of the first drug A inside the first barrel 22 to be visually recognized.

A first gasket 34 is inserted into the first barrel 22, and a proximal end side of the first storage chamber 32 is sealed by the first gasket 34. The first drug A is sealed in the first storage chamber 32. Although not particularly limited, the first drug A can be, for example, a liquid such as water (injection water) or physiological saline for diluting the other second drug B.

The first plunger 24 is inserted from the first opening portion 28 on the proximal end side of the first barrel 22. The first plunger 24 is connected to the first gasket 34. The first plunger 24 may be configured to be attached to the first gasket 34 immediately before use.

The first connection port 30 is a structure for connection to a second connection port 60 (see FIG. 3B) of the second syringe 14 which will be described later and connection of the injection needle 16. The first connection port 30 includes a lock portion 36 extending in a tubular shape from the vicinity of an outer periphery of the first barrel 22 toward the distal end side of the first barrel 22, and a luer tip 38 extending in a tubular shape from the vicinity of a central axis of the first barrel 22 toward the distal end side of the first barrel 22 inside the lock portion 36. The injection needle attachment structure of the first connection port 30 includes the lock portion 36 and the luer tip 38. In the first connection port 30 in an unused state, a blocking member 40 that blocks attachment of the injection needle 16 is disposed between the lock portion 36 and the luer tip 38.

A male screw 42 is formed on an outer peripheral portion 36*a* of the lock portion 36. The male screw 42 is constituted with one or more spiral screw structures. Further, a needle connection screw 44 for screwing and attaching the injection needle 16 is formed on an inner peripheral portion 36*b* of the lock portion 36. The needle connection screw 44 is constituted as a spiral screw structure having the same pitch as the male screw 42.

The luer tip 38 is formed to protrude longer (farther) toward the distal end side in an axial direction than the lock portion 36. A through hole 46 penetrating in the axial direction is formed in the vicinity of the central axis of the luer tip 38. A proximal end side of the through hole 46 is opened to the first storage chamber 32 of the first barrel 22, so that the through hole 46 communicates with the first storage chamber 32. An outer peripheral portion 38*a* of the luer tip 38 is formed in a tapered shape such that an outer diameter gradually decreases toward the distal end side. The outer peripheral portion 38*a* of the luer tip 38 is formed to have an outer diameter smaller than that of the inner peripheral portion 36*b* of the lock portion 36, and a gap 48 is formed between the outer peripheral portion 38*a* and the inner peripheral portion 36*b* of the lock portion 36. The blocking member 40 that blocks entry of a proximal end of the injection needle 16 is disposed in the gap 48.

The blocking member 40 is formed in a cylindrical shape having an outer diameter and an inner diameter that allow the blocking member 40 to be inserted into or positioned in the gap 48. A proximal end portion 40*a* of the blocking member 40 abuts on the distal end of the first barrel 22, and a distal end portion 40*b* of the blocking member 40 extends to the vicinity of the distal end of the lock portion 36. An outer peripheral portion 40*c* of the blocking member 40 is provided with a male screw 50 that can be screwed into (screw-engaged or threadedly engaged with) the needle connection screw 44 of the inner peripheral portion 36*b* of the lock portion 36. The male screw 50 has a screw structure with the same pitch as the needle connection screw 44 and is screwed into (screw-engaged or threadedly engaged with) the needle connection screw 44 to prevent the blocking member 40 from falling off to the distal end side.

An inner peripheral portion 40*d* of the blocking member 40 is formed to have an inner diameter larger than that of the outer peripheral portion 38*a* of the luer tip 38, and the inner peripheral portion 40*d* is separated radially outward of or spaced radially outwardly of the luer tip 38. A columnar gap 52 is formed between the inner peripheral portion 40*d* of the blocking member 40 and the outer peripheral portion 38*a* of the luer tip 38. A width (dimension) in a radial direction of the gap 52 is substantially equal to or slightly smaller than a thickness (dimension in a radial direction) of the inner tubular portion 78 of the second connection port 60 which will be described later.

A first cap 26 is detachably attached to the distal end side of the first connection port 30. The first cap 26 includes a cylindrical main body portion 54 and a sealing member 56 disposed so as to close an inner peripheral side of the main body portion 54. The main body portion 54 includes a twisting portion (screw portion) 54*a* to be screwed into (screw-engaged or threadedly engaged with) the male screw 42 of the outer peripheral portion 36*a* of the lock portion 36. A first cap body portion 54*b* whose diameter is reduced radially inward is formed on the distal end side of the twisting portion 54*a*. A seal storage hole 54*c* having an inner diameter smaller than the inner diameter of the lock portion 36 is formed inside the first cap body portion 54*b*, and an end portion of the sealing member 56 is stored in the seal storage hole 54*c*.

The sealing member 56 is fabricated from an elastically deformable material such as a rubber material, and a distal end portion 56*a* of the sealing member 56 is stored or positioned in the seal storage hole 54*c*. A recess 56*b* engaged with a protrusion (radially inwardly directed protrusion) 54*d* protruding from the seal storage hole 54*c* is formed in the distal end portion 56*a*, and the sealing member 56 is stored in a state where the sealing member 56 is not displaced in the axial direction by the recess 56*b* being engaged with the protrusion 54*d*.

A close contact portion 56*c* formed in a tubular shape is formed on the proximal end side of the sealing member 56. The close contact portion 56*c* is formed in a bottomed cylindrical shape that can be in close contact with the outer peripheral surface of the luer tip 38. Part of a distal end side of the close contact portion 56*c* is formed thick and is compressed in the radial direction by the outer peripheral surface of the luer tip 38 and the seal storage hole 54*c*, so that the close contact portion 56*c* is reliably brought into close contact with the outer peripheral surface of the luer tip 38. The sealing member 56 seals the through hole 46 at the distal end of the luer tip 38 in an airtight and liquid-tight manner. The distal end side of the first storage chamber 32 of the first barrel 22 is sealed by the sealing member 56.

Figure 3A:
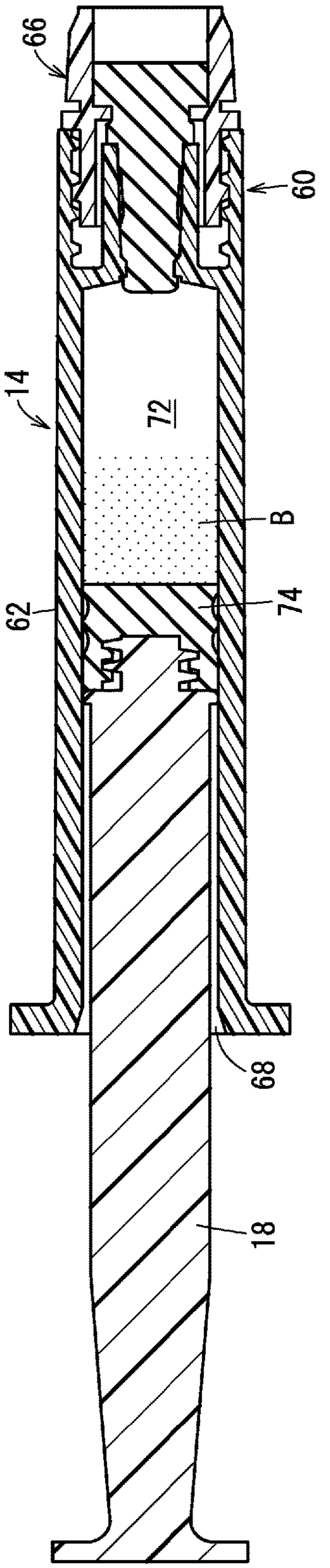
FIG. 3A is a cross-sectional view of a second syringe of FIG. 1.
Figure 3B:
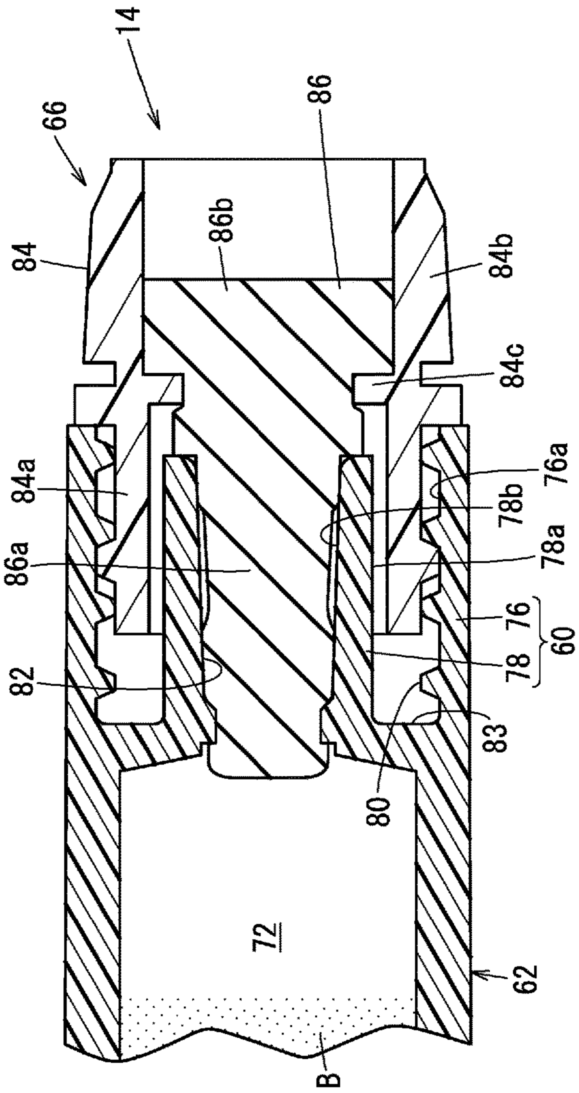
FIG. 3B is an enlarged cross-sectional view of a distal end portion of the second syringe of FIG. 3A.

On the other hand, as illustrated in FIG. 3A, the second syringe 14 includes a second barrel 62, a second plunger 18, and a second cap 66. Among them, the second barrel 62 is formed in a cylindrical shape, a second opening portion 68 is formed on the proximal end side, and a second connection port 60 is formed on the distal end side. Inside of the second barrel 62 is a second storage chamber 72 that stores a drug. A second gasket 74 is inserted into the second barrel 62, and a proximal end side of the second storage chamber 72 is sealed by the second gasket 74. The second barrel 62 is formed with a transparent resin so as to allow a state of the second drug B inside the second barrel 62 to be visually recognized. Although not particularly limited, the second drug B can be, for example, a powder or a liquid.

The second plunger 18 can be inserted from the second opening portion 68 on the proximal end side of the second barrel 62, and the second plunger 18 is connected to the second gasket 74 immediately before use as illustrated in the drawing. The second plunger 18 may be attached to the second gasket 74 in advance.

The second connection port 60 is used for connection to the first connection port 30 (see FIG. 2B) of the first syringe 12. The second connection port 60 includes an outer tubular portion 76 extending in a tubular shape from the vicinity of an outer periphery of the second barrel 62 toward the distal end side of the second barrel 62, and an inner tubular portion 78 extending in a tubular shape from the vicinity of a central axis of the second barrel 62 toward the distal end side of the second barrel 62 inside the outer tubular portion 76.

The outer tubular portion 76 is formed in a cylindrical shape having an inner diameter larger than that of the lock portion 36, and a female screw 80 is formed on an inner peripheral portion 76*a* of the outer tubular portion 76. The female screw 80 is formed with the same number of threads and the same pitch as the male screw 42 formed on the outer peripheral portion 36*a* of the lock portion 36, and the female screw 80 can be screwed into (screw-engaged or threadedly engaged with) the male screw 42.

The inner tubular portion 78 is slightly shorter in the axial direction than the outer tubular portion 76. A communication hole 82 penetrating in the axial direction is formed on the inner peripheral side of the inner tubular portion 78. The proximal end side of the communication hole 82 is opened to a second storage chamber 72 of the second barrel 62, so that the communication hole 82 communicates with the second storage chamber 72. An inner peripheral portion 78*b* of the inner tubular portion 78 is formed in a tapered shape such that an inner diameter gradually decreases toward the proximal end side so as to be in close contact with the outer peripheral portion 38*a* of the luer tip 38. A thickness (dimension in a radial direction) of the inner tubular portion 78 is equal to or slightly larger than the gap 52 between the inner peripheral portion 40*d* of the blocking member 40 and the outer peripheral portion 38*a* of the luer tip 38. A gap 83 is formed between the inner tubular portion 78 and the outer tubular portion 76. The lock portion 36 and the blocking member 40 of the first connection port 30 are inserted into the gap 83.

The second cap 66 is detachably attached to the distal end side of the second connection port 60. The second cap 66 includes a cylindrical main body portion 84 and a seal member 86 disposed so as to close the inner peripheral side of the main body portion 84. The main body portion 84 includes a twisting portion 84*a* to be screwed into (screw-engaged or threadedly engaged with) the female screw 80 of the inner peripheral portion 76*a* of the outer tubular portion 76. A second cap body portion 84*b* that holds the seal member 86 is formed on the distal end side of the twisting portion 84*a*. A protrusion 84*c* protruding inward (radially inwardly) is formed in the second cap body portion 84*b*, and the seal member 86 is held by the second cap body portion 84*b* by the seal member 86 being caught by the protrusion 84*c*.

The seal member 86 is fabricated from an elastically deformable material such as a rubber material, and a distal end portion 86*b* of the seal member 86 is stored or positioned in the second cap body portion 84*b*. A columnar portion 86*a* is formed on the proximal end side of the seal member 86, and the columnar portion 86*a* is inserted into the communication hole 82 of the inner tubular portion 78 to seal the communication hole 82 in an airtight and liquid-tight manner. The distal end side of the second storage chamber 72 of the second barrel 62 is sealed by the seal member 86.

The injection needle 16 includes a needle tube 16*a* and a needle hub 16*b* that supports the needle tube 16*a*. The needle tube 16*a* is fabricated from a metal such as stainless steel, for example, and a needle tip 16*c* capable of puncturing the skin is formed at the distal end of the needle tube 16*a*. The needle hub 16*b* is fabricated from, for example, a resin member, and a needle hole communicating with the inside of the needle tube 16*a* is provided inside the needle hub 16*b*. The needle hole inside the needle hub 16*b* is formed in a shape that can be brought into close contact with the luer tip 38 of the first connection port 30. In addition, a flange portion 16*d* that can be screwed into the needle connection screw 44 of the lock portion 36 is provided at the proximal end of the needle hub 16*b*. The injection needle 16 is provided in a state where the needle tube 16*a* is covered with the needle cap 16*e*.

The syringe set 10 of the present embodiment is configured as described above, and use thereof will be described below.

Figure 4A:
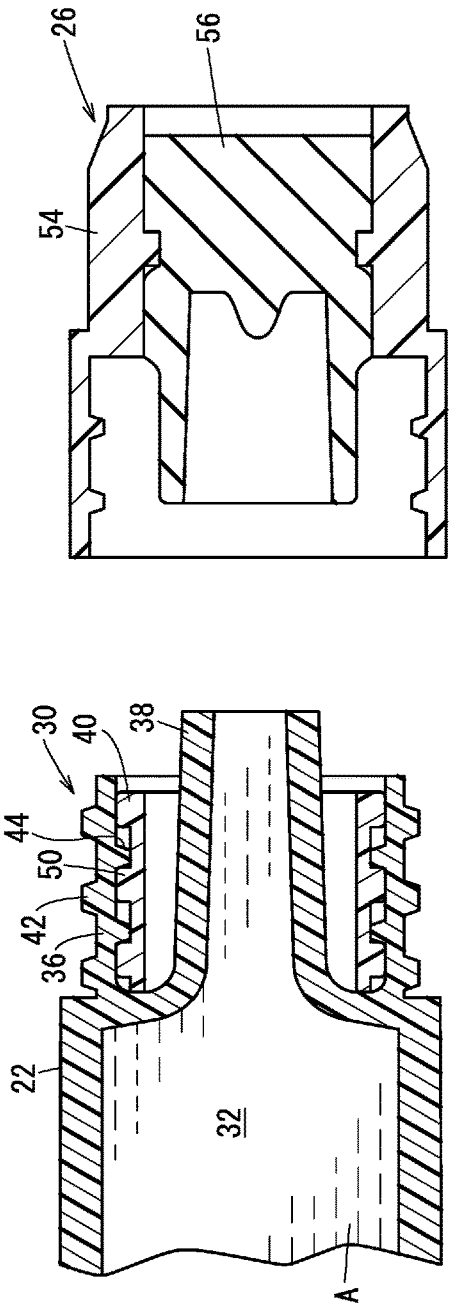
FIG. 4A is a cross-sectional view of a state in which a cap of the first syringe is removed.

The first syringe 12 and the second syringe 14 of the syringe set 10 are removed from the tray 20 of FIG. 1 by a user. Thereafter, as illustrated in FIG. 4A, the user holds the first syringe 12 and rotates the first cap 26 to detach the first cap 26 from the first connection port 30.

Figure 5:
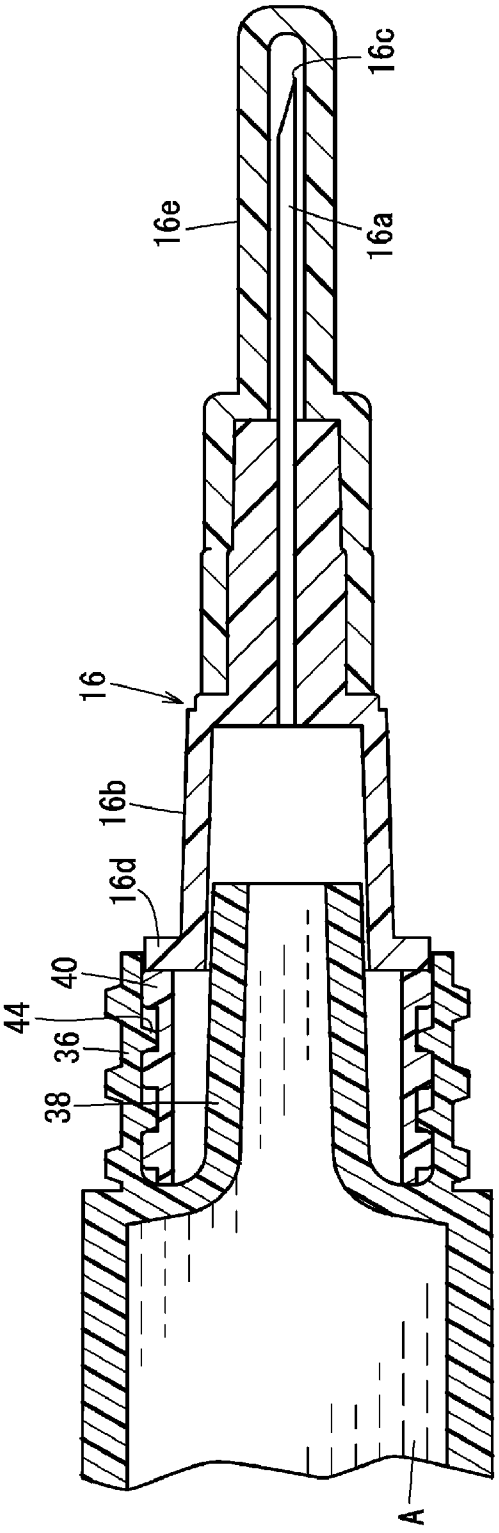
FIG. 5 is a cross-sectional view illustrating action of a blocking member of a first connection port.

When the first cap 26 is removed from the first connection port 30, the lock portion 36 appears or is exposed. In this state, the blocking member 40 is disposed on the inner peripheral side of the lock portion 36. As illustrated in FIG. 5, when the user forgets mixing the first drug A and the second drug B and tries to attach the injection needle 16 to the first connection port 30 of the first syringe 12, the proximal end of the needle hub 16*b* of the injection needle 16 is hindered by the blocking member 40. In order to connect the injection needle 16 to the first connection port 30, it is necessary to screw the flange portion 16*d* of the injection needle 16 to the needle connection screw 44 of the lock portion 36. In the first syringe 12 of the present embodiment, the injection needle 16 is blocked from proceeding by the blocking member 40, and thus the injection needle 16 is blocked from being screwed into the lock portion 36. This results in preventing the user from attaching the injection needle 16 to the first syringe 12 that stores only the first drug A.

Figure 4B:
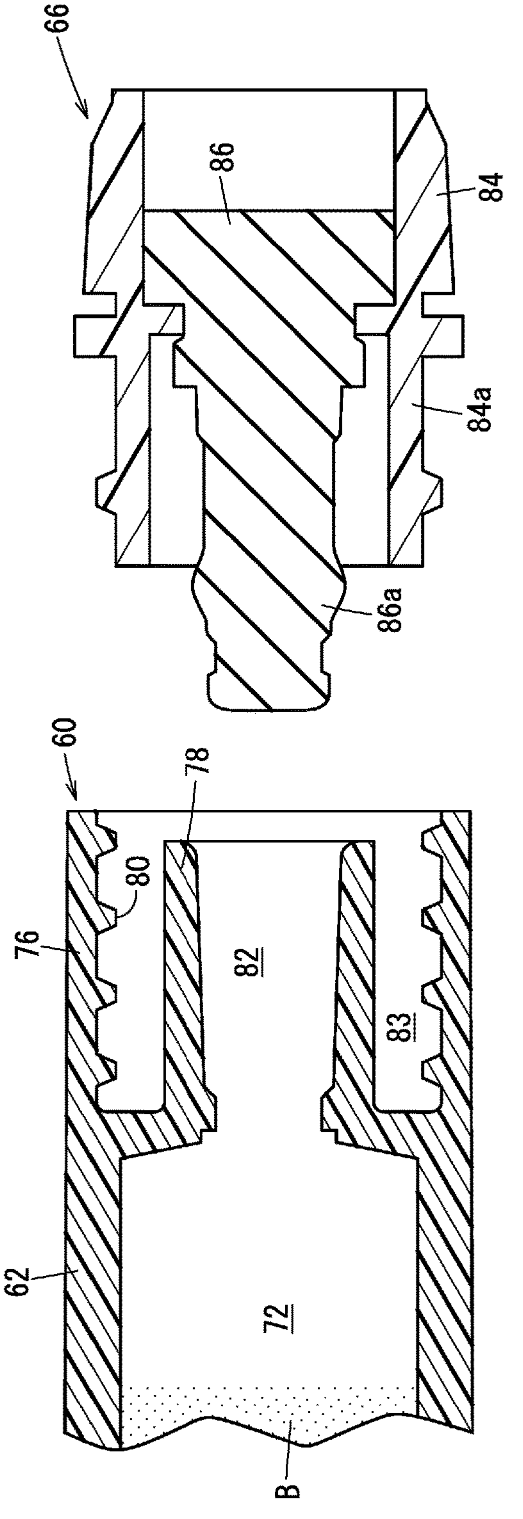
FIG. 4B is a cross-sectional view of a state in which a cap of the second syringe is removed.

Thereafter, as illustrated in FIG. 4B, the user holds the second syringe 14 and rotates the second cap 66 to detach the second cap 66 from the second connection port 60. As a result, the first syringe 12 can be connected to the second syringe 14.

Figure 6:
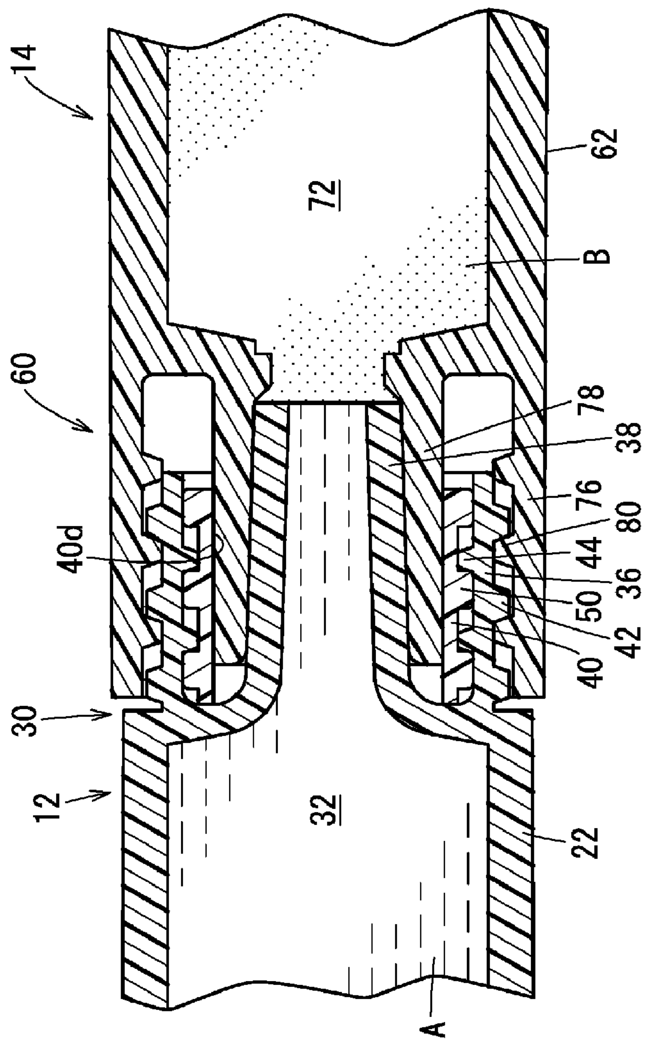
FIG. 6 is a cross-sectional view illustrating a state in which a second connection port is connected to the first connection port and drugs are mixed between the first syringe and the second syringe.

Next, as illustrated in FIG. 6, the user screws the second connection port 60 of the second syringe 14 into the first connection port 30 of the first syringe 12 to connect the first connection port 30 to the second connection port 60. The female screw 80 of the inner peripheral portion 76*a* of the outer tubular portion 76 of the second connection port 60 and the male screw 42 of the outer peripheral portion 36*a* of the lock portion 36 of the first connection port 30 are screwed together, whereby the first connection port 30 is connected to the second connection port 60.

In addition, the luer tip 38 of the first connection port 30 is connected in close contact with inside of the communication hole 82 of the inner tubular portion 78 of the second connection port 60 in a liquid-tight and airtight manner. As a result, the first storage chamber 32 of the first syringe 12 communicates with the second storage chamber 72 of the second syringe 14. The inner tubular portion 78 of the second connection port 60 is inserted into the gap 52 between the blocking member 40 and the luer tip 38, and the blocking member 40 is fitted and joined to the inner tubular portion 78.

Thereafter, the user performs operation of alternately pushing the first plunger 24 (see FIG. 2A) of the first syringe 12 and the second plunger 18 (see FIG. 3A) of the second syringe 14. As a result, the first drug A in the first storage chamber 32 and the second drug B in the second storage chamber 72 are mixed, and preparation of an injection C is completed.

Figure 7:
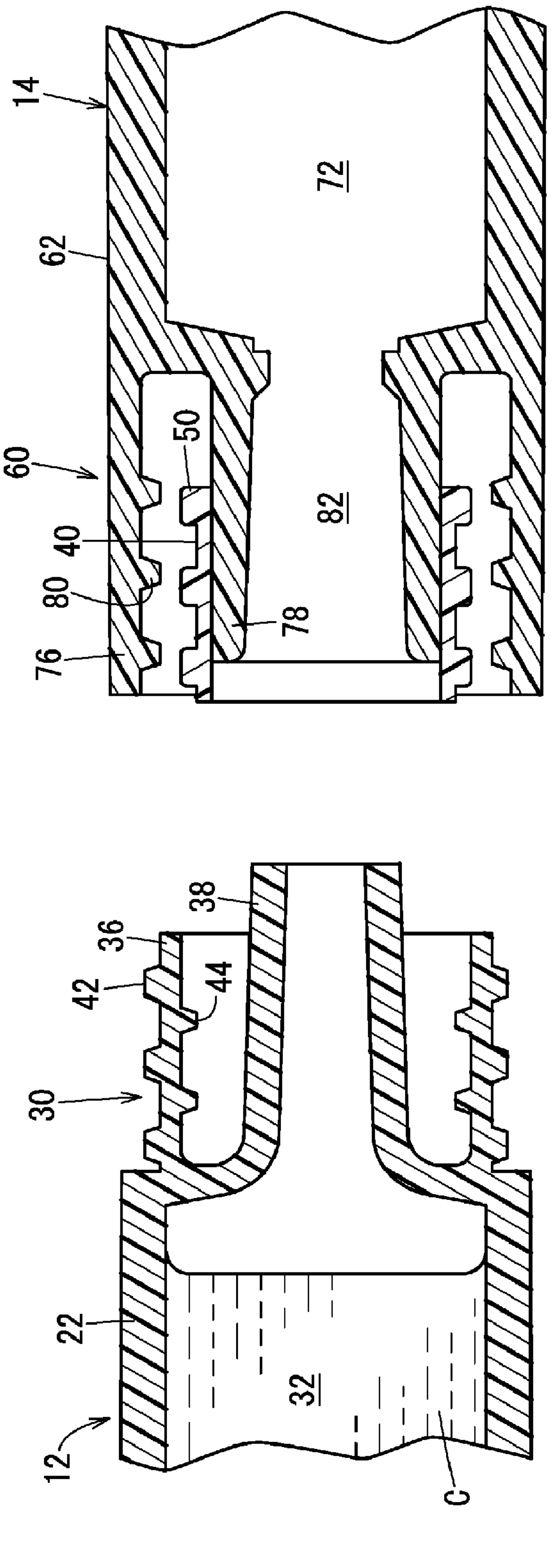
FIG. 7 is a cross-sectional view of a state in which the second connection port is removed from the first connection port after the drugs are mixed.

Next, as illustrated in FIG. 7, after the prepared injection C is stored on the first syringe 12 side, the user rotates the second syringe 14 to detach the second syringe 14 from the first syringe 12. In this event, the blocking member 40 rotates integrally with the inner tubular portion 78 of the second connection port 60. The pitch of the male screw 50 of the blocking member 40 is the same as the pitch of the female screw 80 of the outer tubular portion 76 of the second connection port 60, and thus the blocking member 40 is also detached from the needle connection screw 44 of the inner peripheral portion 36*b* of the lock portion 36 along with release of screwing of the second connection port 60 to the first connection port 30. As a result, the injection needle 16 can be connected to the first connection port 30.

Figure 8:
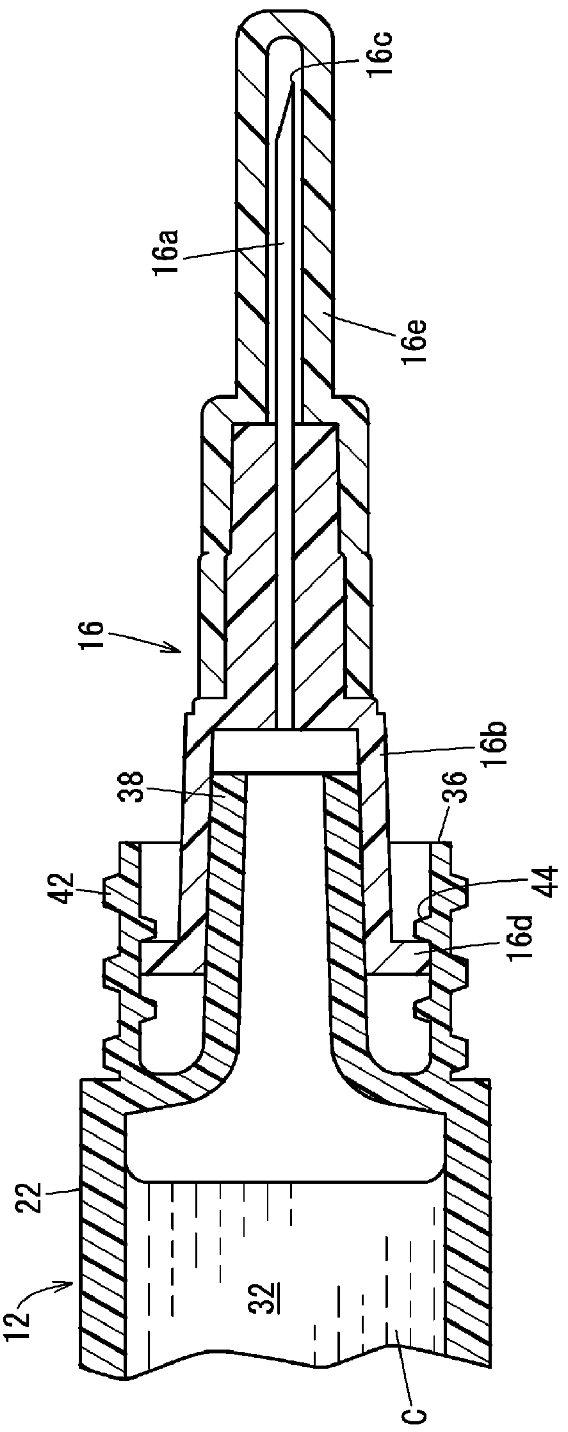
FIG. 8 is a cross-sectional view of a state in which an injection needle is attached to the first connection port.

Next, as illustrated in FIG. 8, the injection needle 16 is screwed into the first connection port 30 of the first syringe 12 to connect the injection needle 16, whereby preparation for administration of the injection C is completed. Thereafter, the user removes the needle cap 16*e* of the injection needle 16, punctures the needle tip 16*c* subcutaneously, and presses the first plunger 24 (see FIG. 2A) to administer the injection C. Thus, administration of the injection C using the syringe set 10 is completed.

The syringe set 10 of the present embodiment has the following effects.

The syringe set 10 of the present embodiment includes the first syringe 12 and the second syringe 14 (drug container). The first syringe 12 includes the first barrel 22 that stores a liquid first drug A, and the first connection port 30 that is provided at the distal end of the first barrel 22 and communicates with inside of the first barrel 22. In addition, the second syringe 14 stores the second drug B and has the second connection port 60 detachable from the first connection port 30. The first connection port 30 includes the injection needle attachment structure to which the injection needle 16 is attached, and the blocking member 40 provided in the injection needle attachment structure to block attachment of the injection needle 16 to the injection needle attachment structure. When the second connection port 60 is connected to the first connection port 30, the blocking member 40 is connected to the second connection port 60 side, and when the second connection port 60 to which the blocking member 40 is connected is detached from the first connection port 30, the blocking member 40 is detached from the first connection port 30 so as to allow the injection needle 16 to be attached to the injection needle attachment structure.

According to the above configuration, the injection needle 16 cannot be attached to the first syringe 12 unless the second connection port 60 is connected to the first connection port 30 and the first drug A of the first syringe 14 and the second drug B of the second syringe 12 are mixed. This can prevent the user from erroneously administering the unprepared first drug A as a result of attaching the injection needle 16 to the first syringe 12 that stores only the first drug A before the drugs are mixed.

In the syringe set 10, the injection needle attachment structure may include the tubular lock portion 36 in which the needle connection screw 44 into which the injection needle 16 is screwed is formed in the inner peripheral portion 36*b,* and the luer tip 38 formed inside the lock portion 36 and having the through hole 46 communicating with the inside of the first barrel 22, and the blocking member 40 may be disposed between the lock portion 36 and the luer tip 38. According to this configuration, it is possible to prevent the injection needle 16 from being screwed into the lock portion 36 by the blocking member 40.

In the syringe set 10, the blocking member 40 is formed in a cylindrical shape, and the outer peripheral portion 40*c* is provided with the male screw 50 as a protrusion to be screwed into the needle connection screw 44 on the inner peripheral side of the lock portion 36. As described above, the blocking member 40 is screwed into the needle connection screw 44, so that it is possible to prevent falling off to the distal end side.

In the syringe set 10 described above, the male screw 42 may be formed on the outer peripheral portion 36*a* of the lock portion 36 of the first connection port 30, and the second connection port 60 may have the outer tubular portion 76 having, on the inner peripheral portion 76*a,* the female screw 80 that can be screwed into the male screw 42 of the outer peripheral portion 36*a* of the lock portion 36, and the inner tubular portion 78 that is formed inside the outer tubular portion 76, has the communication hole 82 communicating with the second storage chamber 72, is inserted between the lock portion 36 and the luer tip 38, and stores the luer tip 38 in the communication hole 82. As a result, the attachment structure of the inner tubular portion 78 and the luer tip 38 is simplified.

In the syringe set 10, the blocking member 40 may be configured such that the inner peripheral portion 40*d* is separated from the luer tip 38, and the inner tubular portion 78 is inserted into the inner peripheral portion 40*d* of the blocking member 40 and joined to the blocking member 40. According to this configuration, when the second connection port 60 is connected to the first connection port 30, the blocking member 40 is fitted and joined to the inner tubular portion 78.

In the syringe set 10 described above, the blocking member 40 may block the vicinity of the distal end of the needle connection screw 44 of the inner peripheral portion 36*b* of the lock portion 36. According to this configuration, the injection needle 16 is reliably prevented from being screwed into the lock portion 36.

In the syringe set 10 described above, the first cap 26 that seals the first syringe 12 may be provided, and the first cap 26 may include the first cap body portion 54*b* having the twisting portion 54*a* to be screwed into the male screw 42 of the outer peripheral portion 36*a* of the lock portion 36, and the sealing member 56 that is supported by the first cap body portion 54*b* and abuts on the luer tip 38 to seal the through hole 46.

In the syringe set 10, the drug container may be the second syringe 14 having the second barrel 62 as the second storage chamber 72 that stores the second drug B.

In addition, the first syringe 12 of the present embodiment is connected to the drug container that stores the second drug B immediately before use, and administration is performed after the liquid first drug A is mixed with the second drug B. The first syringe 12 includes the first barrel 22 that stores the first drug A, and the first connection port 30 provided at the distal end of the first barrel 22 and configured to be connectable to the drug container (second syringe 14). The first connection port 30 is provided with the injection needle attachment structure to which the injection needle 16 is attachable, and the blocking member 40 that is disposed in the injection needle attachment structure and blocks attachment of the injection needle 16 to the injection needle attachment structure. Then, when the second syringe 14 is connected to the first connection port 30, the blocking member 40 is connected to the second syringe 14 side, and when the second syringe 14 to which the blocking member 40 is connected is detached from the first connection port 30, the blocking member 40 is detached from the first connection port 30 so as to allow the injection needle 16 to be attached to the injection needle attachment structure.

According to the first syringe 12 having the above configuration, attachment of the injection needle 16 in a state of only the unmixed first drug A can be blocked by the blocking member 40, so that erroneous administration can be prevented.

Modification of First Embodiment

Figure 2B:
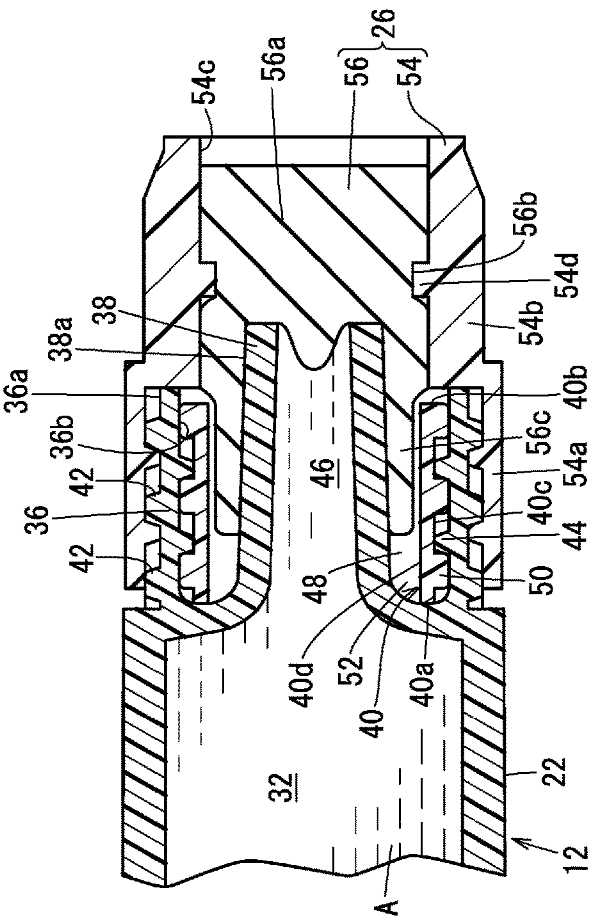
FIG. 2B is an enlarged cross-sectional view of a distal end portion of the first syringe of FIG. 2A.

In the example described with reference to FIG. 2B, the male screw 50 is provided on the outer peripheral portion 40*c* of the blocking member 40, and the male screw 50 of the blocking member 40 is screwed into the needle connection screw 44 of the lock portion 36. However, the present embodiment is not limited to this.

Figure 9:
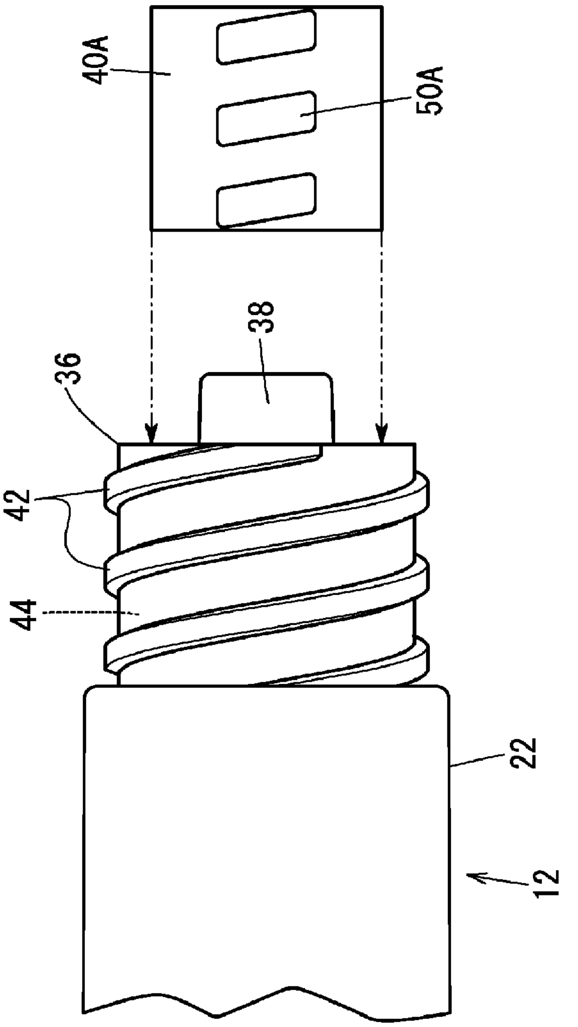
FIG. 9 is a side view of a blocking member according to a modification of the first embodiment.

In other words, as illustrated in a separated state in FIG. 9, an outer peripheral portion 40*c* of a blocking member 40A may be provided with a protrusion 50A that can be screwed into the needle connection screw 44 of the lock portion 36 instead of the male screw 50. In the illustrated embodiment shown by way of example in FIG. 9, the outer peripheral portion 40*c* of the blocking member 40A may be provided with plural protrusions 50A axially spaced apart from one another. The protrusions 50A are provided as protrusions separated from one another so as to occupy only part of the outer peripheral portion 40*c* of the blocking member 40 in a circumferential direction. As illustrated in the drawing, a plurality of protrusions 50A may be provided at the same pitch as the pitch of the needle connection screw 44 in the axial direction, or only one protrusion may be provided in the axial direction.

Also by the blocking member 40A of the present modification, the same effects as those of the blocking member 40 can be obtained.

Second Embodiment

Figure 10:
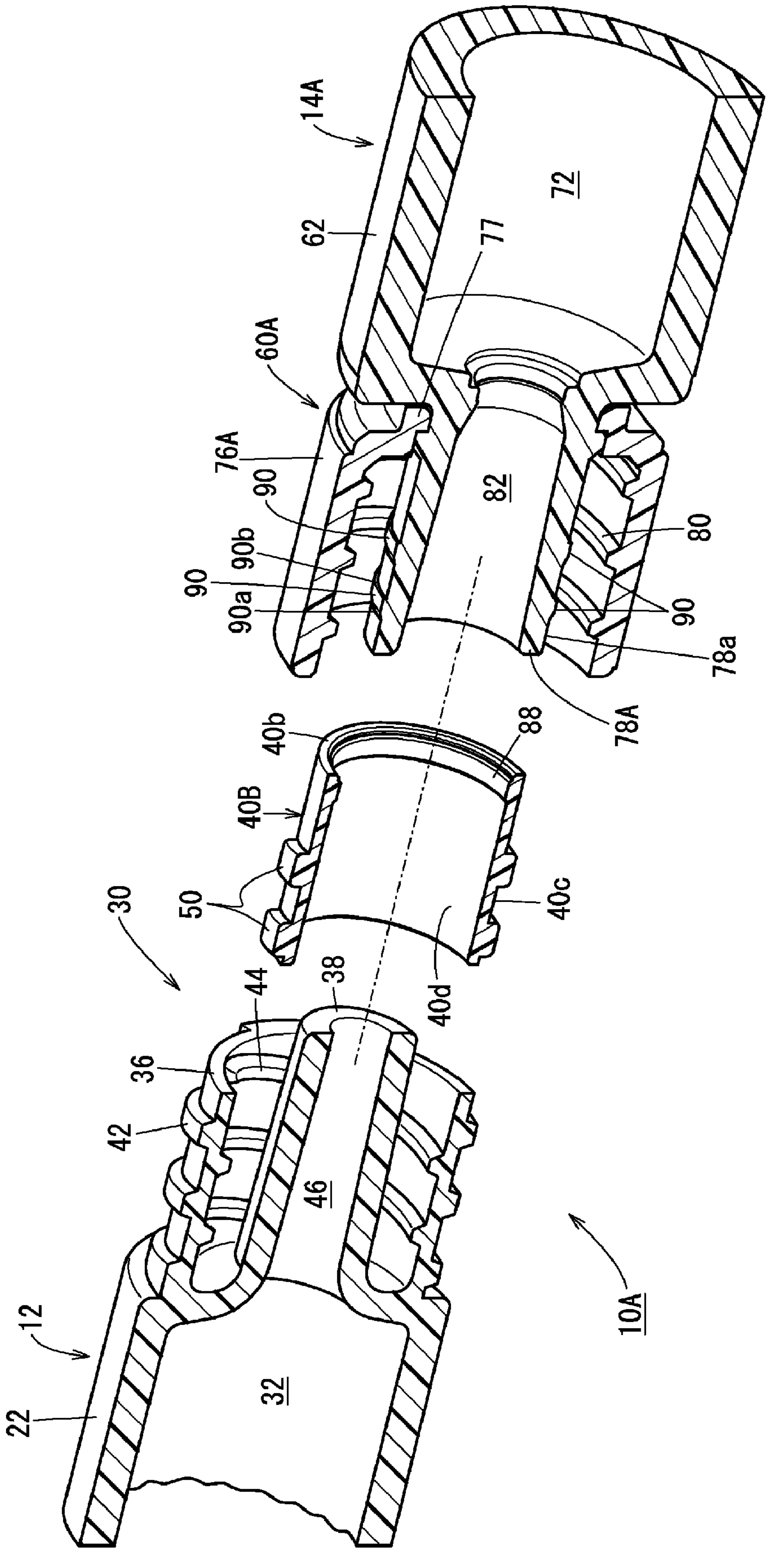
FIG. 10 is an exploded perspective cross-sectional view of a first syringe and a second syringe of a syringe set according to a second embodiment.

As illustrated in FIG. 10, a syringe set 10A of the present embodiment is different from the syringe set 10 described with reference to FIGS. 1 to 9 in that protrusions that can be engaged with each other are provided on an inner peripheral portion 40*d* of a blocking member 40B and an outer peripheral portion 78*a* of an inner tubular portion 78A. In the configuration of the syringe set 10A of the present embodiment, the same components as those of the syringe set 10 of the first embodiment are denoted by the same reference numerals, and the detailed description thereof will be omitted.

As illustrated in FIG. 10, the blocking member 40B includes a first protrusion 88 protruding inward from the inner peripheral portion 40*d*. The first protrusion 88 is provided in the vicinity of a distal end portion 40*b* of the blocking member 40B and is formed in an annular shape along the circumferential direction of the inner peripheral portion 40*d*.

In a second connection port 60A of a second syringe 14A, second protrusions 90 are provided on the outer peripheral portion 78*a* of the inner tubular portion 78A. The second protrusions 90 are annular protrusions protruding outward from the outer peripheral portion 78*a* of the inner tubular portion 78A and are formed in an annular shape along the circumferential direction of the inner tubular portion 78A. A plurality of the second protrusions 90 is provided and they are spaced apart at intervals in the axial direction. The second protrusions 90 have a protrusion height allowing the second protrusions 90 to be engaged with the first protrusion 88 of the blocking member 40B. An inclined surface 90*a* for smooth insertion into the first protrusion 88 is formed on the distal end side of the second protrusion (protrusions) 90. In addition, on the proximal end side of each second protrusion 90, a vertical surface 90*b* that stands vertically to the axial direction is provided so that the second protrusions are not easily separated or detached from the first protrusion 88. The second protrusions 90 do not have to be formed in an entire region in the circumferential direction, and only one second protrusion may be provided in the axial direction.

Although not particularly limited, in the second connection port 60A of the present embodiment, the outer tubular portion 76A may be molded separately from the second syringe 14A. The outer tubular portion 76A is assembled to the second syringe 14A by being fitted to a fitting structure 77 provided at the distal end of the second barrel 62 and in the vicinity of a root of the inner tubular portion 78A. The outer tubular portion 76A may be integrally molded with the second syringe 14A similarly to the outer tubular portion 76 (FIG. 3B) of the first embodiment.

The syringe set 10A of the present embodiment is configured as described above, and action thereof will be described below.

Figure 11:
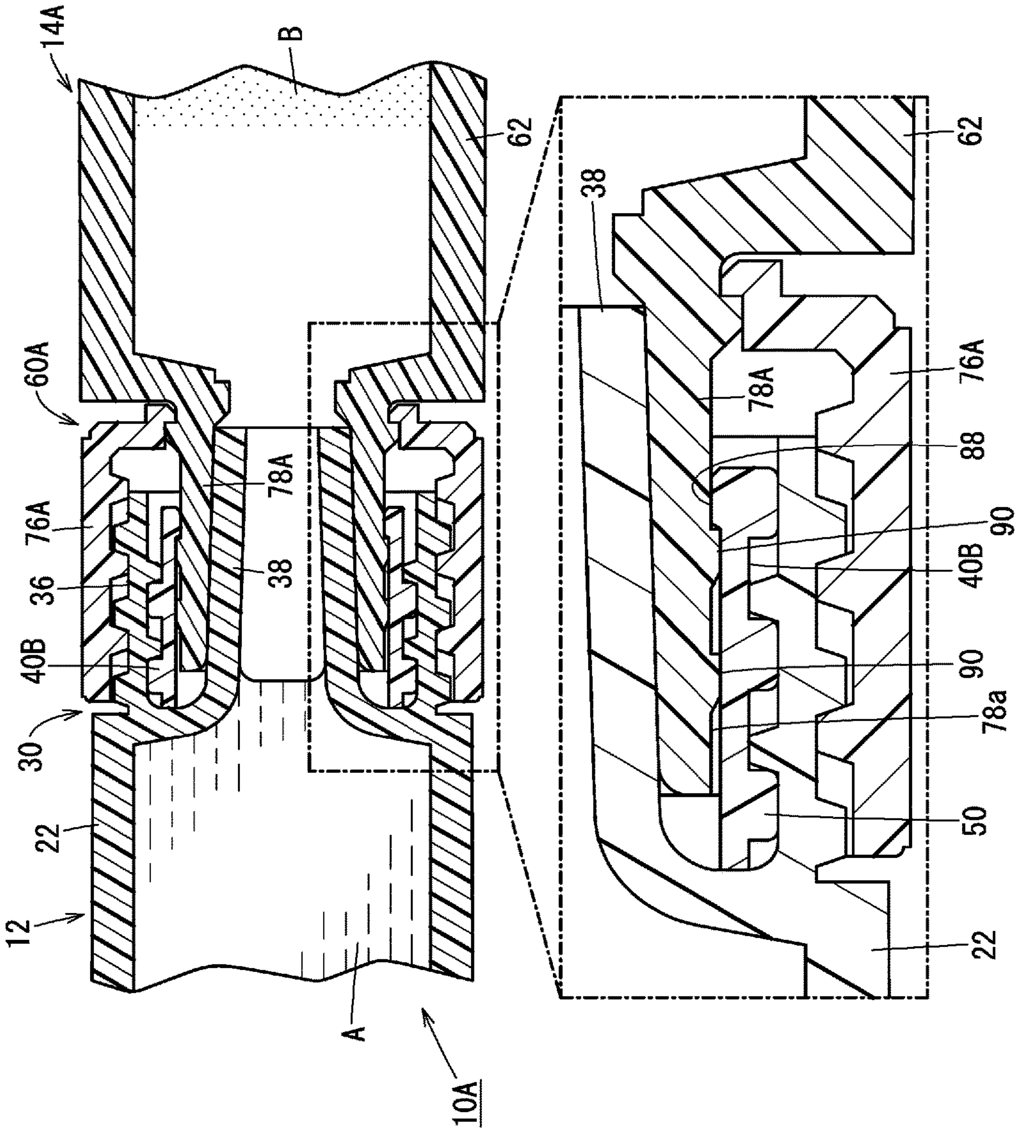
FIG. 11 is a cross-sectional view of a state in which a second connection port is connected to a first connection port of FIG. 10.

As illustrated in FIG. 11, when the second connection port 60A is connected to the first connection port 30, the inner tubular portion 78A and the second protrusions 90 of the inner tubular portion 78A are inserted into the proximal end side of the first protrusion 88 of the blocking member 40B. When the second connection port 60A is removed from the first connection port 30, the blocking member 40B is pulled out together with the inner tubular portion 78A by the second protrusions 90 being engaged with the first protrusion 88 of the blocking member 40B. Accordingly, the blocking member 40B can be reliably removed together with the second connection port 60A.

The syringe set 10A of the present embodiment has the following effects.

In the syringe set 10A of the present embodiment, protrusions (the first protrusion 88 and the second protrusions 90) that can be engaged with each other are formed on the inner peripheral portion 40*d* of the blocking member 40B and the outer peripheral portion 78*a* of the inner tubular portion 78A.

This causes the inner tubular portion 78A to be engaged with the blocking member 40B, so that the blocking member 40B can be more reliably removed.

In the syringe set 10A, the protrusions (the first protrusion 88 and the second protrusions 90) may be formed in an annular shape extending in the circumferential direction. Accordingly, the blocking member 40B can be more reliably removed together with the inner tubular portion 78A.

An uneven structure of the present embodiment is not limited to the annular first protrusion 88 and the second protrusions 90 and may be configured by a combination of an annular groove and a protrusion.

Third Embodiment

Figure 12:
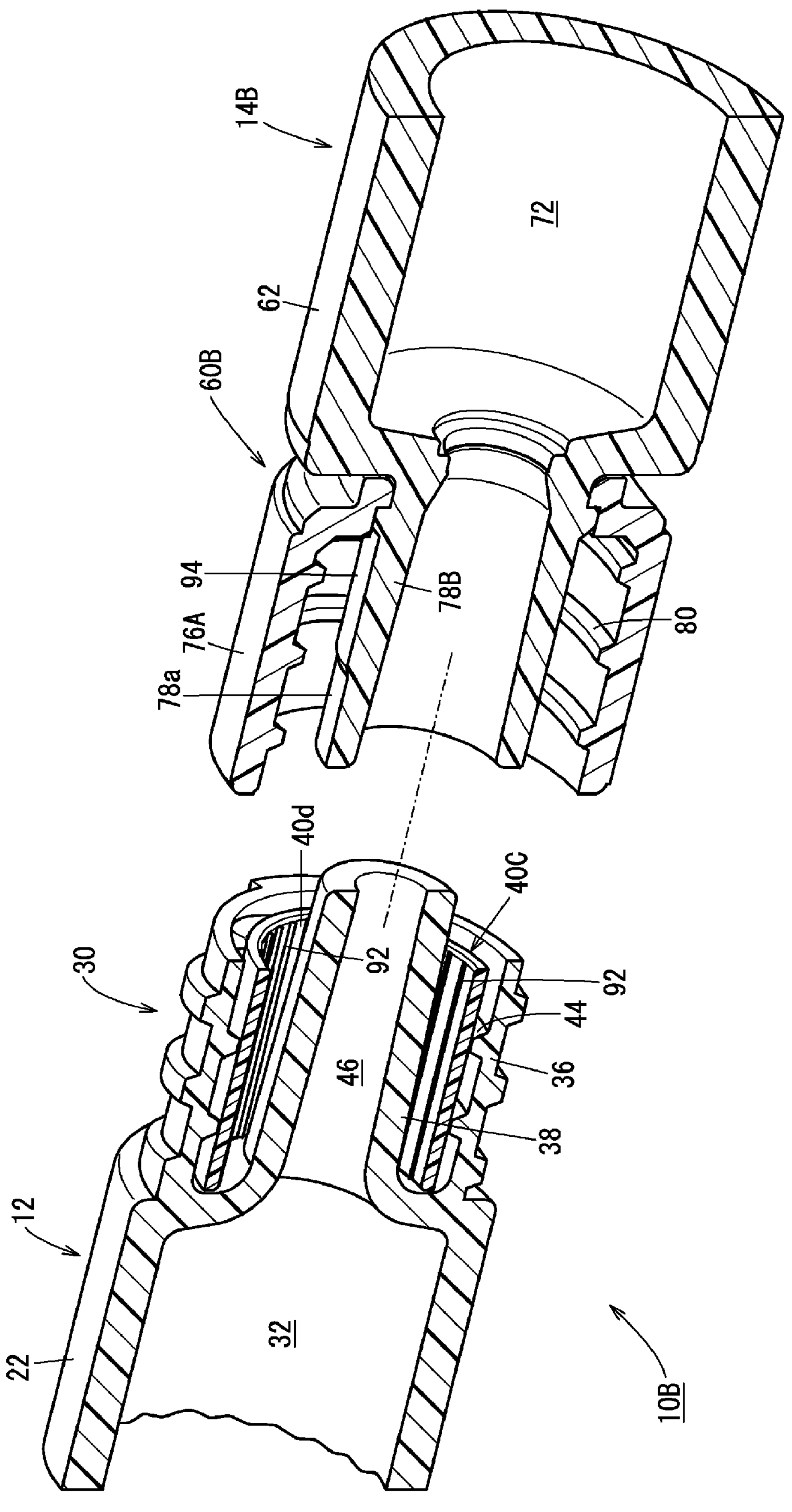
FIG. 12 is a perspective cross-sectional view of a first syringe and a second syringe of a syringe set according to a third embodiment.

As illustrated in FIG. 12, a syringe set 10B of the present embodiment is provided with uneven structures that can be engaged with each other on an inner peripheral portion 40*d* of a blocking member 40C and an outer peripheral portion 78*a* of the inner tubular portion 78B. The uneven structure of the present embodiment is different from the syringe set 10A described with reference to FIG. 10 in including vertical ribs 92 extending in the axial direction formed in the inner peripheral portion 40*d* of the blocking member 40C. In the configuration of the syringe set 10B of the present embodiment, the same components as those of the syringe set 10A of the second embodiment are denoted by the same reference numerals, and a detailed description of such components will not be repeated.

As illustrated in FIG. 12, the vertical ribs 92 extending in the axial direction are formed on the inner peripheral portion 40*d* of the blocking member 40C. A plurality of vertical ribs 92 is disposed at a constant pitch in the circumferential direction. On the other hand, an enlarged diameter portion 94 protruding radially outward is provided on a proximal end side of the inner tubular portion 78B in the outer peripheral portion 78*a* of the inner tubular portion 78B of the second syringe 14B.

The syringe set 10B of the present embodiment is configured as described above, and action thereof will be described below.

In the syringe set 10B, when the second connection port 60B is connected to the first connection port 30, the inner tubular portion 78B is inserted into the inner peripheral portion 40*d* of the blocking member 40C. When the enlarged diameter portion 94 of the inner tubular portion 78B is pushed into the inner peripheral portion 40*d* of the blocking member 40C, the inner tubular portion 78B and the blocking member 40C are joined by fitting.

Thereafter, when the second connection port 60B is rotated and removed from the first connection port 30, the blocking member 40C is detached together with the inner tubular portion 78B. In this event, the vertical ribs 92 of the blocking member 40C are caught, engaged or contacted by the inner tubular portion 78B to exert stronger joining force in a rotation direction, and thus, the blocking member 40C rotates integrally with the inner tubular portion 78B, so that the blocking member 40C can be removed more reliably.

As described above, the syringe set 10B of the present embodiment includes the vertical ribs 92 extending in the axial direction as the uneven structure, so that the blocking member 40C can be reliably removed using the needle connection screw 44 of the lock portion 36.

The vertical ribs 92 may be formed on the inner tubular portion 78B side. In addition, the vertical ribs 92 may be formed on both the inner peripheral portion 40*d* and the inner tubular portion 78B of the blocking member 40C.

Fourth Embodiment

Figure 13:
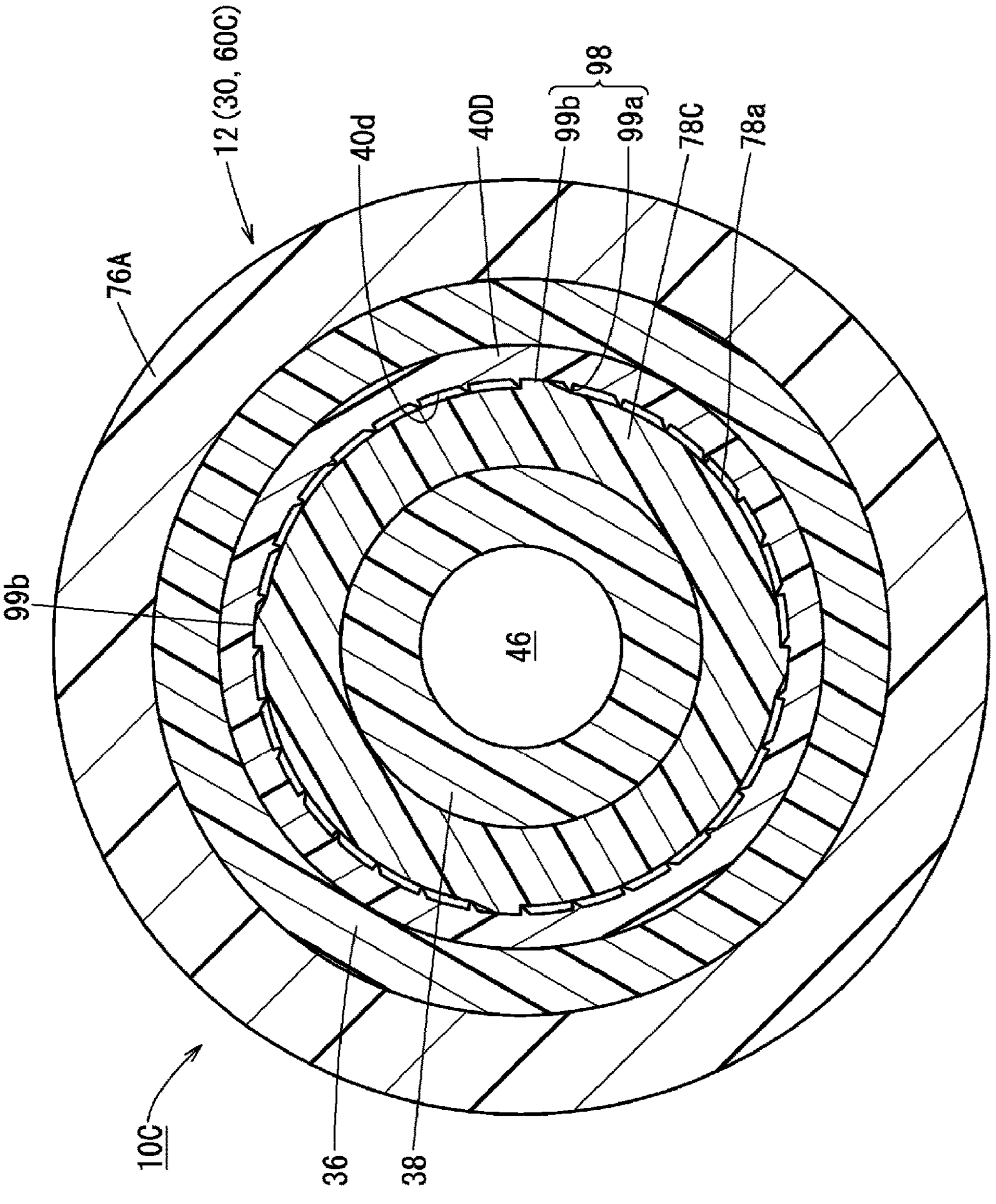
FIG. 13 is a cross-sectional view of a state in which a first connection port is connected to a second connection port in a syringe set according to a fourth embodiment.

As illustrated in FIG. 13, a syringe set 10C of the present embodiment is provided with uneven structures that can be engaged with each other on the inner peripheral portion 40*d* of a blocking member 40D and the outer peripheral portion 78*a* of an inner tubular portion 78C. FIG. 13 illustrates a cross section cut perpendicularly to the axial direction in a state where the second connection port 60C is connected to the first connection port 30. The uneven structure of the present embodiment is different from the syringe set 10A described with reference to FIG. 10 in including a ratchet structure 98 that rotates the blocking member 40D only in a predetermined direction. In the configuration of the syringe set 10C of the present embodiment, the same components as those of the syringe set 10A of the second embodiment are denoted by the same reference numerals, and a detailed description of such components will not be repeated.

As illustrated in FIG. 13, in the blocking member 40D of the present embodiment, first ratchet protrusions 99*a* extending in the axial direction are formed in an inner peripheral portion 40*d*. A plurality of first ratchet protrusions 99*a* are provided at regular intervals in the circumferential direction. An inclined surface is formed on one side of a side portion of the first ratchet protrusion 99*a*.

On the other hand, second ratchet protrusions 99*b* are formed at a plurality of positions in the circumferential direction on the outer peripheral portion 78*a* of the inner tubular portion 78C of the second connection port 60C. One side portion of the second ratchet protrusion 99*b* is formed with an inclined surface.

When the second connection port 60C is screwed into the first connection port 30, the first ratchet protrusions 99*a* and the second ratchet protrusions 99*b* come into contact with each other on their inclined surfaces while being elastically deformed in a thickness direction. This enables the user to perform operation of screwing the second connection port 60C.

On the other hand, when the second connection port 60C is rotated in a removal direction, the first ratchet protrusions 99*a* and the second ratchet protrusions 99*b* are engaged with each other. As a result, the blocking member 40D rotates integrally with the inner tubular portion 78C and is displaced in a direction away from the first connection port 30 by the needle connection screw 44. As a result, the blocking member 40D is detached from the first connection port 30 together with the inner tubular portion 78C.

As described above, the syringe set 10C of the present embodiment includes, as the uneven structure, the ratchet structure 98 that rotates the blocking member 40D only in a direction of separating from the needle connection screw 44 of the lock portion 36. Accordingly, the blocking member 40D can be reliably removed from the first connection port 30.

Fifth Embodiment

Figure 14:
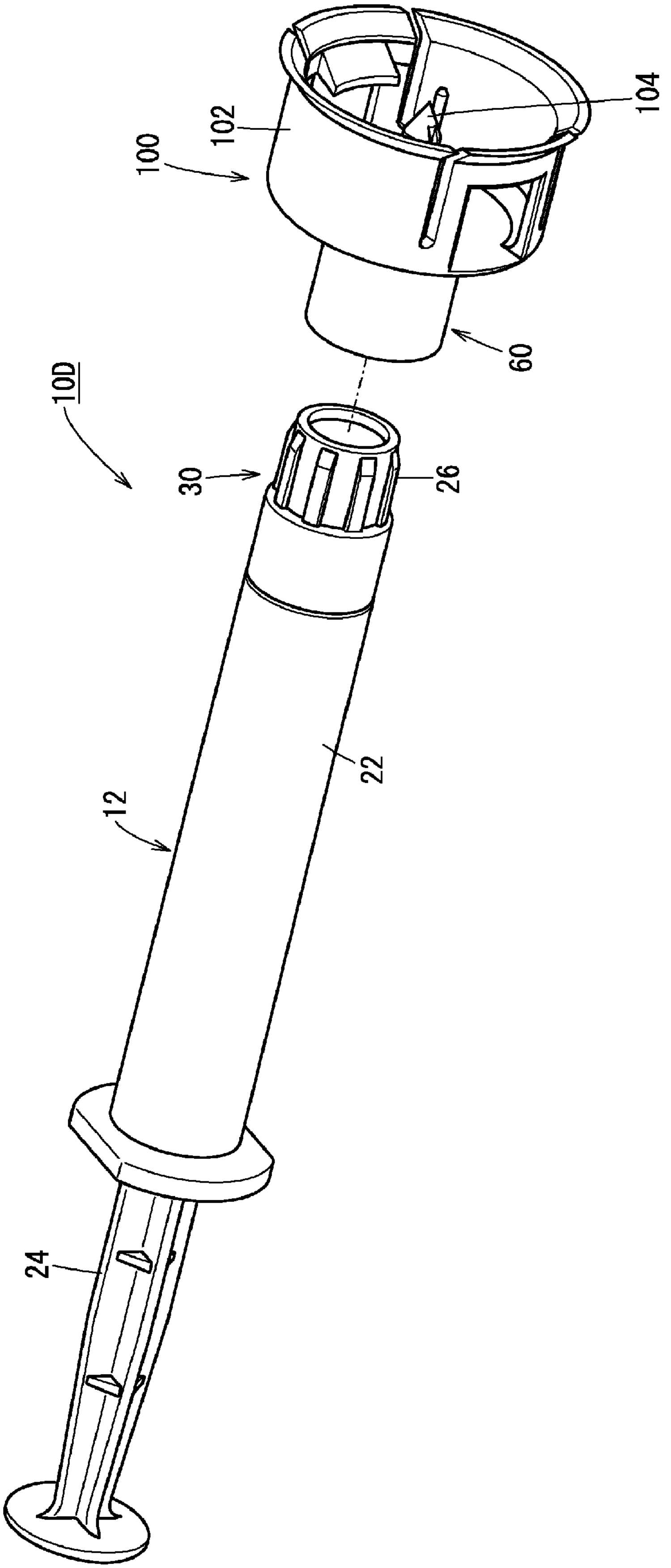
FIG. 14 is a perspective view of a first syringe and a vial adapter of a syringe set according to a fifth embodiment.

As illustrated in FIG. 14, a syringe set 10D (set) of the present embodiment includes the first syringe 12 and a vial adapter 100 (connector). The syringe set 10D is applied in a case where a vial is used as a drug container instead of the second syringe 14. In the configuration of the syringe set 10D of the present embodiment, the same components as those of the syringe set 10 described with reference to FIGS. 1 to 9 are denoted by the same reference numerals, and a detailed description of such components will not be repeated.

As illustrated in the drawing, the vial adapter 100 is a member connected to a bottle opening of the vial container and includes a connection portion 102 for connecting to the bottle opening of the vial container, a connection needle 104 penetrating a rubber stopper of the vial container, and a second connection port 60 for connecting to the first syringe 12.

Figure 15:
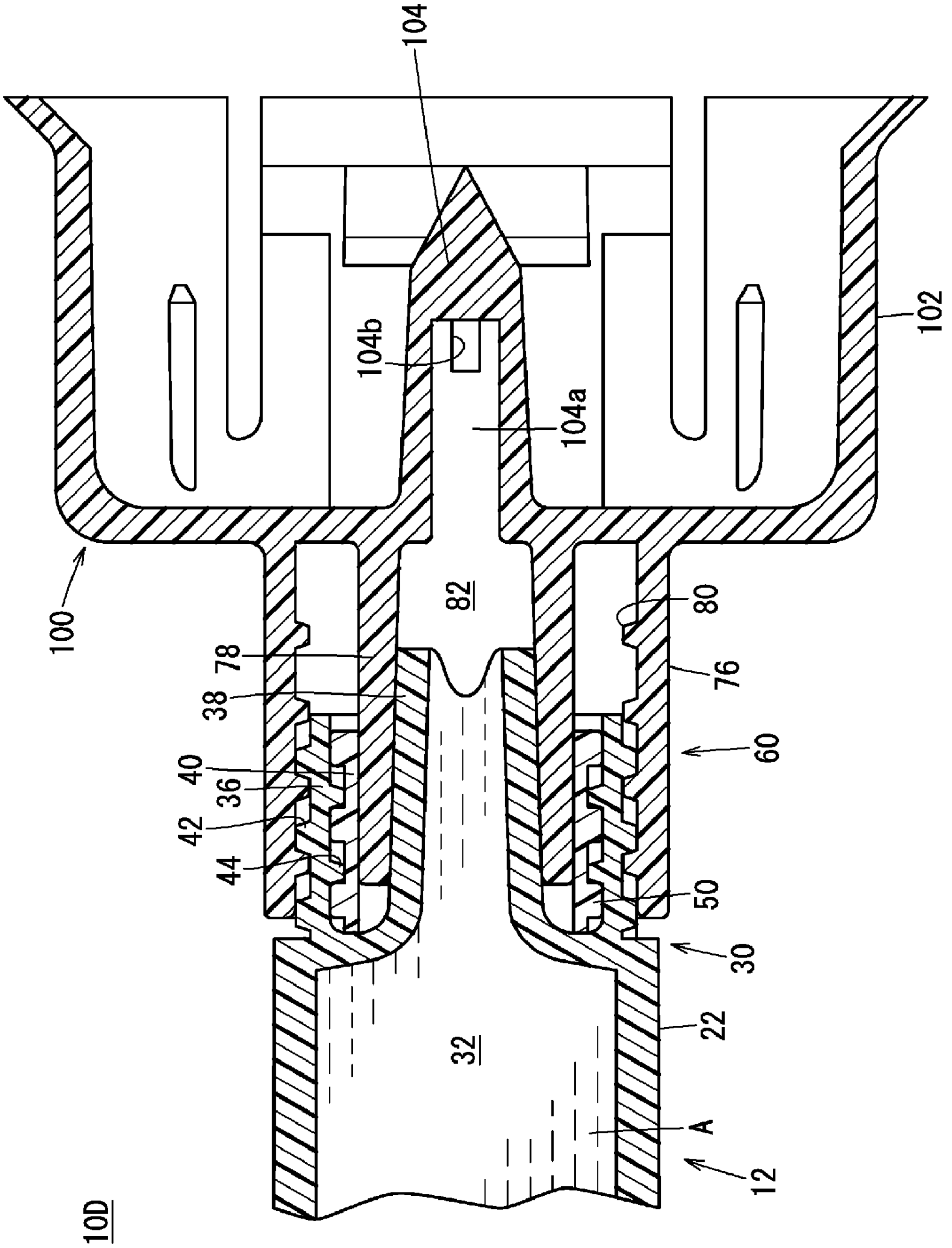
FIG. 15 is a cross-sectional view of a state in which the vial adapter is connected to the first syringe of FIG. 14.

As illustrated in FIG. 15, the connection needle 104 is provided in the vicinity of a central axis of the connection portion 102 and protrudes to one end side of the connection portion 102. A cavity portion 104*a* is provided at the center of the connection needle 104. The cavity portion 104*a* communicates with an outer peripheral side of the connection needle 104 through a window portion 104*b* on a side portion. When the vial container is punctured with the connection needle 104, the cavity portion 104*a* communicates with inside of the vial container through the window portion 104*b*.

The second connection port 60 extends from an opposite side of the connection needle 104 across the connection portion 102. A communication hole 82 of the second connection port 60 communicates with the cavity portion 104*a* of the connection needle 104.

The syringe set 10D of the present embodiment is used by connecting the vial adapter 100 to a vial container and further connecting the first syringe 12 to the vial adapter 100. When the second connection port 60 of the vial adapter 100 is connected to the first connection port 30 of the first syringe 12, the blocking member 40 of the first connection port 30 is joined to the inner tubular portion 78 of the second connection port 60.

Then, when the vial adapter 100 is removed from the first syringe 12 after preparation of the injection, the blocking member 40 is detached from the first connection port 30 together with the vial adapter 100. As a result, the injection needle 16 can be connected to the first syringe 12.

As described above, the syringe set 10D of the present embodiment also prevents erroneous administration due to forgetting of mixing of an injection.

The detailed description above describes embodiments of a syringe set, a syringe, and a set to be used for preparing an injection by mixing drugs before use, and a method, representing examples of the new syringe set, syringe, set and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe set comprising:

a first syringe including a barrel having an inside in which is stored a liquid first drug, the first syringe including a first connection port at a distal end of the barrel, the first connection port communicating with the inside of the barrel;

a drug container having an inside in which is stored a second drug, the drug container including a second connection port that is connectable to and detachable from the first connection port of the first syringe;

the first connection port of the first syringe including an injection needle attachment structure configured to be attached to an injection needle, and a blocking member disposed in the injection needle attachment structure and configured to block attachment of the injection needle to the injection needle attachment structure when the blocking member is disposed in the injection needle attachment structure, the blocking member being detachable from the first connection port to remove the blocking member from the injection needle attachment structure and permit attachment of the injection needle to the injection needle attachment structure;

the blocking member being connectable to a part of the second connection port when the second connection port is connected to the first connection port;

the blocking member being detachable from the first connection port when the second connection port to which the blocking member is connected is detached from the first connection port, thereby allowing the injection needle to be attached to the injection needle attachment structure;

the injection needle attachment structure comprising: a tubular lock portion that includes an inner peripheral portion at which is located a needle connection screw into which the injection needle is to be screwed; and a luer tip formed inside the tubular lock portion and having a through hole communicating with the inside of the barrel;

the blocking member being disposed between the tubular lock portion and the luer tip;

the tubular lock portion of the first connection port possessing an outer peripheral portion at which is located a male screw; and the second connection port comprising:

an outer tubular portion possessing an inner periphery at which is located a female screw that is configured to be screwed into the male screw on the outer peripheral portion of the tubular lock portion; and an inner tubular portion positioned inside the outer tubular portion, the inner tubular portion including a communication hole communicating with the inside of the drug container, the inner tubular portion being positioned between the tubular lock portion and the luer tip when the second connection port is connected to the first connection port, and the luer tip being positioned in the communication hole when the second connection port is connected to the first connection port.

2. The syringe set according to claim 1, wherein the blocking member is a cylindrically-shaped blocking member possessing an outer peripheral portion, the outer peripheral portion of the cylindrically-shaped blocking member including an outwardly projecting protrusion configured to be screwed into the needle connection screw at the inner peripheral portion of the tubular lock portion.

3. The syringe set according to claim 1, wherein the blocking member possesses an inner peripheral surface that is separated from the luer tip, the inner tubular portion of the second connection port being located inwardly of the inner peripheral surface of the blocking member and joined to the blocking member when the second connection port is connected to the first connection port.

4. The syringe set according to claim 3, wherein the inner tubular portion possesses an outer peripheral surface, the outer peripheral surface of the inner tubular portion and the inner peripheral surface of the blocking member each including uneven structures, the uneven structures on the inner peripheral surface of the blocking member and the uneven structures on the outer peripheral surface of the inner tubular portion engaging each other when the second connection port is connected to the first connection port.

5. The syringe set according to claim 4, wherein the uneven structures on the outer peripheral surface of the inner tubular portion include a circumferentially extending annular protrusion, and the uneven structures on the inner peripheral surface of the blocking member include a circumferentially extending annular protrusion.

6. The syringe set according to claim 4, wherein the uneven structures on the inner peripheral surface of the blocking member include an axially extending vertical rib.

7. The syringe set according to claim 4, wherein the uneven structures on the inner peripheral surface of the blocking member and on the outer peripheral surface of the inner tubular portion form a ratchet structure that rotates the blocking member only in a direction in which the blocking member is detached from the needle connection screw of the tubular lock portion.

8. The syringe set according to claim 1, wherein the blocking member blocks a distal end portion of the needle connection screw in the inner peripheral portion of the tubular lock portion to prevent a flange portion of the injection needle from screwing into the needle connection screw in the inner peripheral portion of the tubular lock portion when the blocking member is disposed in the injection needle attachment structure.

9. The syringe set according to claim 1, further comprising a cap that seals the first syringe, wherein the cap comprises: a cap body portion having a twisting portion to be screwed into the male screw on the outer peripheral portion of the tubular lock portion; and a sealing member that is supported by the cap body portion and abuts on the luer tip to seal the through hole.

10. The syringe set according to claim 1, wherein the drug container is a second syringe having a barrel as a second storage chamber that stores the second drug.

11. The syringe set according to claim 1, further comprising a tray provided with a plurality of spaced-apart accommodation recesses, the first syringe being located in a first one of the accommodation recesses and the drug container being located in a second one of the accommodation recesses.

12. The syringe set according to claim 1, wherein the needle connection screw is configured to receive a flange portion of the injection needle after the blocking member is detached from the first connection port, the blocking member covering a part of the needle connection screw of the injection needle attachment structure so that the flange portion of the injection needle is unable to be screwed into the needle connection screw of the injection needle attachment structure.

13. The syringe set according to claim 1, wherein the needle connection screw is configured to receive a flange portion of the injection needle after the blocking member is detached from the first connection port, the blocking member including a screw part that is screwed into the needle connection screw of the injection needle attachment structure so that the flange portion of the injection needle is unable to be screwed into the needle connection screw of the injection needle attachment structure.

14. A combination of a syringe and a drug container in which is stored a drug immediately before use and that is used for administration after a liquid drug inside the syringe is mixed with the drug stored in the drug container, the syringe comprising:

a barrel in which is stored the liquid drug;

a first connection port at a distal end of the barrel and configured to be connected to the drug container so that the syringe is connected to the drug container and the liquid drug stored in the barrel of the syringe mixes with the drug stored in the drug container;

the first connection port including an injection needle attachment structure configured to be attached to an injection needle, and a blocking member disposed in the injection needle attachment structure and configured to block attachment of the injection needle to the injection needle attachment structure when the blocking member is disposed in the injection needle attachment structure, the blocking member being detachable from the first connection port to remove the blocking member from the injection needle attachment structure and permit attachment of the injection needle to the injection needle attachment structure;

the blocking member being connectable to the drug container when the drug container is connected to the syringe; and the blocking member being detachable from the first connection port when the drug container to which the blocking member is connected is detached from the first connection port, thereby allowing the injection needle to be attached to the injection needle attachment structure;

the injection needle attachment structure comprising: a tubular lock portion that includes an inner peripheral portion at which is located a needle connection screw into which the injection needle is to be screwed; and a luer tip formed inside the tubular lock portion and having a through hole communicating with an inside of the barrel;

the blocking member being disposed between the tubular lock portion and the luer tip; and the tubular lock portion of the first connection port possessing an outer peripheral portion at which is located a male screw;

the drug container comprising:

a second connection port that is connectable to and detachable from the first connection port of the syringe; and the second connection port comprising: an outer tubular portion possessing an inner periphery at which is located a female screw that is configured to be screwed into the male screw on the outer peripheral portion of the tubular lock portion when the second connection port is connected to the first connection port; and an inner tubular portion positioned inside the outer tubular portion, the inner tubular portion including a communication hole communicating with the inside of the drug container, the inner tubular portion being positioned between the tubular lock portion and the luer tip when the second connection port is connected to the first connection port, and the luer tip being positioned in the communication hole when the second connection port is connected to the first connection port.

15. The combination according to claim 14, wherein the needle connection screw is configured to receive a flange portion of the injection needle after the blocking member is detached from the injection needle attachment structure, the blocking member including a screw part that is screwed into the needle connection screw of the injection needle attachment structure so that the screw part of the blocking member is in engagement with the needle connection screw of the injection needle attachment structure and so that the flange portion of the injection needle is unable to be screwed into the needle connection screw of the injection needle attachment structure while the screw part of the blocking member is in engagement with the needle connection screw of the injection needle attachment structure.

16. The combination according to claim 14, wherein the tubular lock portion is an axially extending tubular lock portion that projects in a distal direction, and further comprising a cap that includes a male screw that is in engagement with the screw part on the outer peripheral surface of the tubular lock portion, the cap also including a sealing member that abuts an open end of the luer tip that is in communication with the through hole in the luer tip to seal the open end of the luer tip.

17. A method comprising:

connecting a syringe having an inside in which is stored a liquid first drug and a drug container having an inside in which is stored a second drug;

the syringe comprising an injection needle attachment structure comprising: a tubular lock portion that includes an inner peripheral portion at which is located a needle connection screw into which an injection needle is to be screwed; and a luer tip formed inside the tubular lock portion and having a through hole communicating with the inside of the syringe, the syringe also comprising a blocking member disposed between the tubular lock portion and the luer tip to block attachment of the injection needle to the injection needle attachment structure by virtue of the blocking member being contacted by a portion of the injection needle, the drug container comprising: an outer tubular portion possessing an inner periphery at which is located a female screw; and an inner tubular portion positioned inside the outer tubular portion, the inner tubular portion including a communication hole communicating with the inside of the drug container;

the connecting of the syringe to the drug container including engaging the female screw on the inner periphery of the outer tubular portion with a male screw on an outer periphery portion of the tubular lock portion and positioning the inner tubular portion of the drug container between the tubular lock portion and the luer tip of the syringe while also positioning the luer tip in the communication hole to communicate the inside of the drug container with the inside of the syringe to mix the first drug and the second drug;

disconnecting the drug container and the syringe from one another while the mixed first and second drugs are in the inside of the syringe so that the drug container and the syringe are separated from one another, the disconnecting of the drug container and the syringe from one another causing the blocking member to be removed from the injection needle attachment structure; and connecting the injection needle to the syringe by causing the portion of the injection needle to engage the injection needle attachment structure, whereby a needle tube of the injection needle communicates with the inside of the syringe so that the mixed first and second drugs can flow into the needle tube.

18. The method according to claim 17, wherein the blocking member covering a part of the needle connection screw before the disconnecting of the drug container and the syringe from one another, the disconnecting of the drug container and the syringe from one another exposing the needle connection screw, and the connecting of the injection needle to the syringe including a flange of the injection needle being screwed into the needle connection screw of the injection needle attachment structure.

* * * * *